(12) United States Patent
Di Berardino et al.

(10) Patent No.: US 8,460,683 B2
(45) Date of Patent: Jun. 11, 2013

(54) **PROTEIN OR GLYCOPROTEIN FROM *HALIOTIS MIDAE* AND ITS USE AS AN IMMUNOTHERAPY AGENT**

(75) Inventors: Luigi Di Berardino, Milan (IT); Oreste Vittore Brenna, Milan (IT)

(73) Assignee: ABC Co S.r.l., Colleferro (RM) (IT)

( * ) Notice: Subject to any disclaimer, the term of this patent is extended or adjusted under 35 U.S.C. 154(b) by 184 days.

(21) Appl. No.: 12/920,659

(22) PCT Filed: Mar. 3, 2009

(86) PCT No.: PCT/EP2009/001499
§ 371 (c)(1),
(2), (4) Date: Nov. 24, 2010

(87) PCT Pub. No.: WO2009/109359
PCT Pub. Date: Sep. 11, 2009

(65) Prior Publication Data
US 2011/0077209 A1    Mar. 31, 2011

(30) Foreign Application Priority Data

Mar. 4, 2008   (IT) ............................. MI2008A0357

(51) Int. Cl.
*A61K 38/17*      (2006.01)
*A61K 39/35*      (2006.01)
*C07K 14/435*     (2006.01)

(52) U.S. Cl.
USPC .................. 424/278.1; 530/350; 530/395

(58) Field of Classification Search
None
See application file for complete search history.

(56) References Cited

U.S. PATENT DOCUMENTS

| | | | | |
|---|---|---|---|---|
| 4,839,293 A | * | 6/1989 | Cantor et al. | 435/357 |
| 2007/0025915 A1 | * | 2/2007 | Cuttitta et al. | 424/1.49 |

FOREIGN PATENT DOCUMENTS

WO    WO 2004089405 A1 * 10/2004

OTHER PUBLICATIONS

Di Berardino et al., "Immune tolerance induced in heterologous (mouse/rat) PCA by a new protein purified from *Haliotis midae*" Allergy, vol. 63, No. suppl. 88, 2008, p. 613.
Lopata et al., "Characteristics of hypersensitivity reactions and identification of a unique 49 kd IgE-binding protein (Hal-m-1) in abalone (*Haliotis midae*)" Journal of Allergy and Clinical Immunology, vol. 100, No. 5, Nov. 1, 1997, p. 642-648.

\* cited by examiner

*Primary Examiner* — Jeffrey E Russel
(74) *Attorney, Agent, or Firm* — Lucas & Mercanti, LLP

(57) ABSTRACT

Disclosed is a protein or glycoprotein obtainable from a crude extract of *Haliotis midae*, with a molecular weight of approx. 30 kDa and an isoelectric point of around 4.3-4.5, possessing passive cutaneous anaphylaxis-inhibiting activity.

6 Claims, 2 Drawing Sheets

SEQUENCE LISTING

<160> NUMBER OF SEQ ID NOS: 1

<210> SEQ ID NO 1
<211> LENGTH: 9
<212> TYPE: PRT
<213> ORGANISM: Haliotis midae

<400> SEQUENCE: 1

Gly Pro Ala Gly Lys Glu Gly Asp Asn
1               5

PROTEIN OR GLYCOPROTEIN FROM *HALIOTIS MIDAE* AND ITS USE AS AN IMMUNOTHERAPY AGENT

This application is a U.S. national stage of PCT/EP2009/001499 filed on Mar. 3, 2009 which claims priority to and the benefit of Italian Application No. MI2008A000357 filed on Mar. 4, 2008, the contents of which are incorporated herein by reference.

The present invention relates to a protein or glycoprotein extractable from *Haliotis midae* and its use as an agent able to prevent the symptoms of allergic disorders and induce preventive, aspecific tolerance of allergic inflammation.

BACKGROUND TO THE INVENTION

The cornerstones of treatment for allergic disorders are:
1. environmental prevention,
2. symptomatic drugs,
3. specific desensitizing immunotherapy.

The latter treatment is usually carried out by administering the offending allergens for long periods of time.

US 20040228850, GB 2400556 and WO 2004089405 (McEwen) disclose the use of beta-glucuronidase extracted from the marine mollusc *Haliotis midae* (South African abalone) as an enhancer for desensitizing treatment with allergens.

EP 1228767, in the Applicant's name, discloses the use of beta-glucuronidase alone, not in combination with allergens, to treat immune and allergic disorders and as an agent able to stimulate the production of Interleukin 12.

DESCRIPTION OF THE INVENTION

Figure 1:
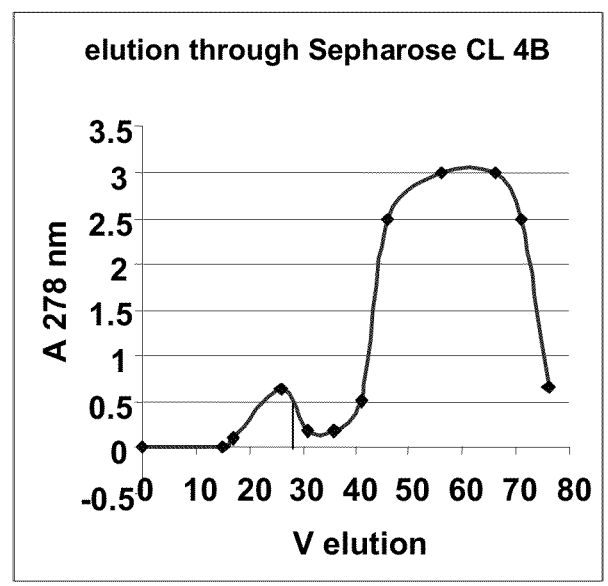
FIG. 1 shows the elution through Sepharose® CL4B of the main peak obtained after chromatography on a Bio-Gel P6 column of the lyophilized form of the raw extract from the sea mollusk *Haliotis midae*.

A novel protein or glycoprotein extractable from *Haliotis midae* has now been found which inhibits anaphylaxis and prevents allergic inflammation. The protein or glycoprotein according to the invention can therefore be used as an antiallergic drug. The invention therefore also relates to pharmaceutical compositions which include the novel protein or glycoprotein as active ingredient.

Throughout the present description, the term "protein" is intended to mean a protein and/or a glycoprotein.

The protein of the invention can be obtained from a crude extract of *Haliotis midae* available on the market in the form of a slightly pigmented lyophilisate, which in aqueous solution buffered to a neutral pH takes on a beige colour, which is darker or lighter depending on its concentration. The solution, for example in 20 mM sodium phosphate buffer at pH 6.9, is centrifuged to remove the undissolved material and eluted through a chromatographic column containing a resin suitable to separate a (lipo)polysaccharide constituent with a high molecular weight. At least two distinct gel filtration chromatography steps will preferably be used, preferably on resins such as poly([allyldextran]-co-N,N'-methylenebisacrylamide): a first step with a resin which has a theoretical fractionation range between 1500 and 10 kDa, marketed under the name of Sephacryl S300 HR®, and a second step with a resin which has a theoretical fractionation range between 100 and 1 kDa, marketed under the name of Sephacryl S 100 HR®.

This elution produces a substantially pure form of the protein with immunostimulating activity, which has a molecular weight of approx. 30 kDa and an isoelectric point of around 4.3-4.5.

This protein can obviously be purified by procedures alternative or complementary to gel filtration, such as the use of ion-exchange resins, hydroxyapatite, electrophoresis systems, and any other known method applicable to protein purification.

The activity of the protein has been evaluated with the mouse/rat passive cutaneous anaphylaxis inhibition test (mr-PCAinib). This method is considered predictive of clinical usefulness; in fact, cutaneous anaphylaxis in the rat induced by specific mouse IgEs is the typical expression of the damage caused by allergic inflammation.

The immunological target of the protein according to the invention which induces tolerance has also been identified in vitro. Increased production of IFN-γ, increased production of IL-10 and suppression of IL-13 production have been evidenced using cultures of adherent cells originating from mononuclear cells isolated from the blood of allergic subjects stimulated with the specific antigen.

This interference with the production of said cytokines may explain the clinical efficacy of the protein of the invention.

For the intended therapeutic uses, the protein can be administered parenterally, for example subcutaneously, or transdermally, suitably formulated with conventional techniques and excipients. The dosages will be determined on the basis of the pre-clinical documentation and phase 1 and 2 clinical trials, and can vary within a wide range, typically between 0.1 μg and 10 mg per dose unit, to be repeated at weekly or monthly intervals.

The invention is described in greater detail in the Examples below.

Example 1

The raw extract from the sea mollusc *Haliotis midae* (South African abalone) in a lyophilized form was obtained from Seravac (Cape Town, South Africa).

The lyophilized raw material (150 mg) was dissolved in 5 mL of 0.1 M sodium phosphate buffer (pH 6.86), and centrifuged at 5,000×g×15 min. to eliminate any undissolved material. The supernatant was eluted on a Bio-Gel P6 chromatographic column (2×16 cm), to remove some pigments. The main peak, 8 mL is collected; four mL of this peak (10 mgP/mL) are successively eluted on a Sepharose® CL 4B (2.5×15 cm; Vtot=74 mL) column, equilibrated with in 0.1 M sodium phosphate buffer, pH 6.86 (FIG. 1).

The first fraction collected, well separated from the proteinaceous material, was negative to the biuret reagent and positive to the phenol-sulphuric acid reagent (Dubois test).

The second peak was divided in three fractions and the central one was retained. The same fraction obtained from four identical elutions was pooled and lyophilized.

Figure 2:
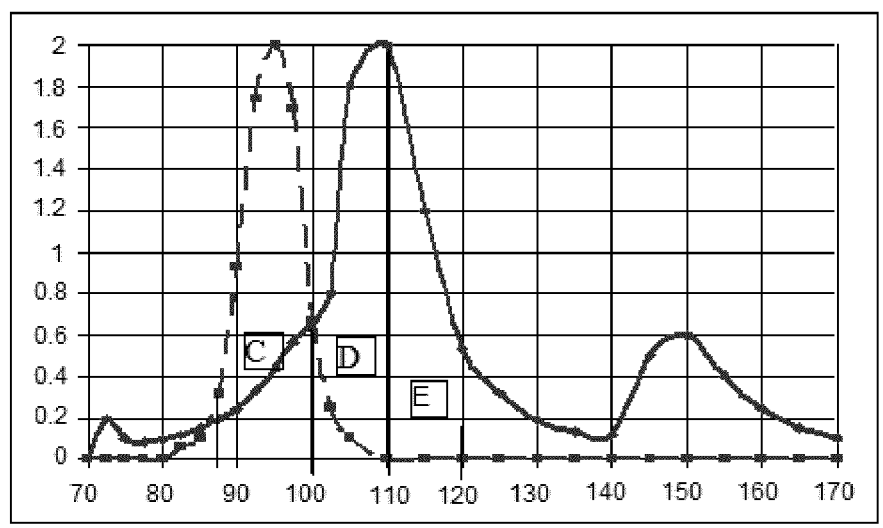
FIG. 2 shows the beta-glucuronidase activity of fractions obtained after chromatography on a Sephacryl S300 HR column.
Figure 3:
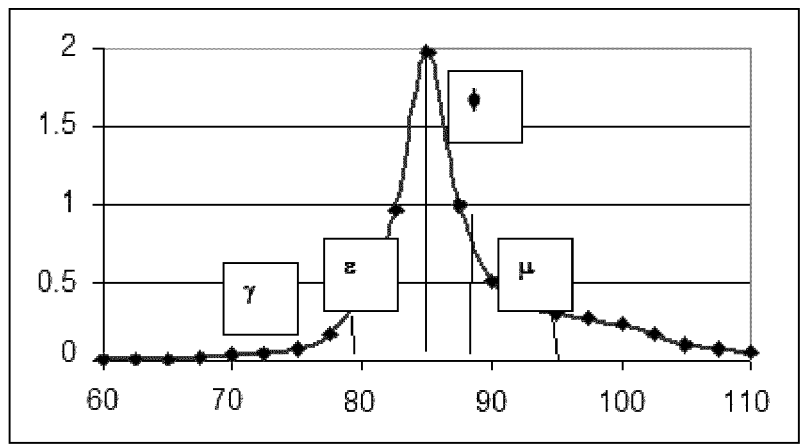
FIG. 3 shows the beta-glucuronidase activity of Fraction E.

Two hundred mg of lyophilizate were dissolved in 5 mL of distilled water and eluted on a Sephacryl S300 HR column (2 cm×50 cm) using a 20 mM sodium phosphate buffer, pH 6.86 The presence of beta-glucuronidase activity was checked every three fractions (2.5 mL each) (dotted line in FIG. 2). Fraction E, free from any beta-glucuronidase activity, was lyophilized and successively eluted on a Sephacryl S100 column (2×50 cm) using a 20 mM sodium phosphate buffer, pH 6.86 (FIG. 3).

The protein present in the fraction ε was found to possess the immunostimulant activity.

Figure 4:
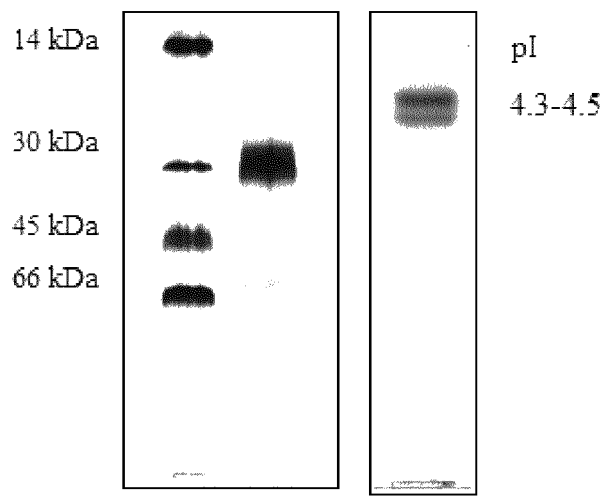
FIG. 4 shows the SDS-PAGE (left) and the isoelectrofocusing separation (right) of the isolated protein fraction.

FIG. 4 shows (left) the SDS-PAGE (7.5% gel) and (right) the isoelectrofocusing separation (range 3.5-10) of the isolated protein fraction.

The purity of the fraction, at around 30 kDa of molecular weight, present in two bands of similar intensity with a pH of 4.3 and 4.5 can be assumed to be >98%, as the MW standard proteins (lysozyme, carbonic anhydrase, ovalbumin and bovine serum albumin) was present in 5 µg amount each.

The protein of the invention is characterized by:
a) a molecular weight under denaturing conditions of about 30 kDa;
b) an isoelectric point in the range of about pH 4-5, in particular about 4.3-4.5;
c) an amino acid composition substantially as reported in the following Table (protein was hydrolyzed by 6 N HCl for 24 hours);
d) an amino acid terminal sequence defined by GPAGKEGDN, SEQ ID NO:1 by a one letter code and Gly-Pro-Ala-Gly-Lys-Glu-Gly-Asp-Asn, SEQ ID NO:1 by a three letter code.

TABLE

Amino acid composition of the 30 kDa protein from *Haliotis midae*:

| Amino acid | % |
| --- | --- |
| Alanine | 3.78 |
| Arginine | 12.78 |
| Aspartic acid | 14.11 |
| Glutamic acid | 11.38 |
| Glycine | 5.49 |
| Histidine | 2.79 |
| Isoleucine | 4.94 |
| Leucine | 4.60 |
| Lysine | 2.29 |
| Methionine | 0.00 |
| Phenylalanine | 9.59 |
| Proline | 6.81 |
| Serine | 5.05 |
| Threonine | 5.58 |
| Tyrosine | 4.80 |
| Valine | 6.01 |

Example 2

Mouse/Rat Cutaneous Anaphylaxis Inhibition

Female Balb/c mice are the species of choice for the immunisation, and SD rats are the species of choice for the passive cutaneous anaphylaxis test.

| Experimental protocol | |
| --- | --- |
| Animals used: | Challenge animals: |
| Balb/c mice (donors) | SD rats (receivers). |
| Sex and age on arrival: | Sex and age on arrival: |
| females, 4 weeks | females, 8-12 weeks. |
| Quarantine and acclimatisation: | Quarantine and acclimatisation: |
| 1 week | 1 week |
| Health status: | Health status: |
| SPF | SPF |
| Number of animals: | Number of animals: |
| 40 | 10 |

Balb/c mice were divided at random into 10 groups, consisting of four mice per cage.

The animals supplied were housed in isolators with a controlled environment (SPF), placed in a room conditioned to a T° of 20-22° C. and RH of 55-60%, given unlimited access to sterilised food pellets and filtered, sterilised water, and placed in groups of 4 in polycarbonate cages with a steel grid.

STEP 1

The mice were sensitised on days $T_0$, $T_{14}$ and $T_{28}$ with 0.25 ml [containing 20 µg of ovoalbumin (OVA)+1 mg aluminium hydroxide] administered intraperitoneally to each mouse. The control animals were treated at the same times with the vehicle.

The animals were treated intradermally at time $T_{21}$ with 0.1 ml of a solution consisting of diluent buffer at pH 5.9 and the test compounds.

An intracardiac blood sample was taken from every mouse in each group at $T_{30}$, and the serum collected was pooled for the next step.

An intracardiac blood sample was taken from the mice in the last two sub-groups at $T_{37}$, and the serum collected was pooled for the next step.

STEP 2

Evaluation of sensitisation by heterologous mouse-rat passive cutaneous anaphylaxis (PCA).

100 µl of scalar dilutions of the pool of serum collected at the end of step 1 was inoculated into the dorsal derma of a pre-shaved rat.

The scalar dilutions used for the evaluation were: positive control; 1:1; 1:20; 1:40; 1:60; 1:80; 1:100; 1:120.

The positive control was the serum at the dilution of 1:1.

0.5 ml (containing 200 µg of OVA and 10 mg/ml of Evans blue) was subsequently (after 24 hours) injected into the caudal vein of the rat.

The mice are deemed to be sensitised if the PCA titre is >1:80 (ie. the last dilution which produces a stain with a diameter greater than 7 mm).

The immunisation programme involves the following steps:

day 0: (time $0=T_0$)—Priming.

The OVA antigen is inoculated and the first intraperitoneal immunisation is given to each mouse.

day 14: ($T_{14}$)—First booster dose.

The second immunisation is given 14 days after the first:

day 21: ($T_{21}$)—Treatments of the different groups studied.

day 28: ($T_{28}$)—Second booster dose.

The third immunisation is given 2 weeks after the second.

day 30: ($T_{30}$)—Blood samples taken to check antibody titre.

If the antibody titre is adequate (dilution 1,1000 OD>1.00), the PCA test is performed.

The animals will be divided into 4 groups (1 control and 3 experimental groups, which in turn are divided into sub-groups). (4 mice per group/sub-group).

Control Group 1

Treatment Group 2 (Protein According to the Invention)

Different sub-groups for each type of treatment day 21 ($T_{21}$): Treatments

All the mice will be treated on the 21st day with 0.1 ml containing the different protein fractions, using the doses and administration routes specified for the type of group to which they belong.

day 30: ($T_{30}$)—Intracardiac whole blood samples taken from each mouse to obtain the immune serum of all groups.

The IgE's specific for OA are determined by the ELISA and PCA method according to Phase 2.

A single treatment with 300 µg/mouse, performed on animals sensitised 7 days before a booster dose, was sufficient to inhibit the allergic response completely.

The invention claimed is:

1. An isolated substantially pure protein or glycoprotein obtainable from a crude extract of *Haliotis midae*, with a molecular weight of approx. 30 kDa and isoelectric point of around 4-5, possessing passive cutaneous anaphylaxis-inhibiting activity.

2. An isolated protein or glycoprotein as claimed in claim 1 obtainable by gel filtration steps.

3. The isolated protein or glycoprotein of claim 1, wherein:
 a) a molecular weight under denaturing conditions is about 30 kDa;
 b) an isoelectric point is in the range of about pH 4.3-4.5;
 c) an amino acid composition is substantially as reported in the following Table,

| Amino acid | % |
|---|---|
| Alanine | 3.78 |
| Arginine | 12.78 |
| Aspartic acid | 14.11 |
| Glutamic acid | 11.38 |
| Glycine | 5.49 |
| Histidine | 2.79 |
| Isoleucine | 4.94 |
| Leucine | 4.60 |
| Lysine | 2.29 |

-continued

| Amino acid | % |
|---|---|
| Methionine | 0.00 |
| Phenylalanine | 9.59 |
| Proline | 6.81 |
| Serine | 5.05 |
| Threonine | 5.58 |
| Tyrosine | 4.80 |
| Valine | 6.01 | wherein the isolated protein or glycoprotein was hydrolyzed by 6 N HCl for 24 hours; and
 d) an amino terminal sequence is defined by Gly-Pro-Ala-Gly-Lys-Glu-Gly-Asp-Asn, SEQ ID NO:1 by a three letter code.

4. Pharmaceutical compositions containing the isolated protein or glycoprotein as claimed in claim 1 as the active ingredient.

5. A method for preventing symptoms of allergic disorders and for inducing preventive, aspecific tolerance of allergic inflammation, said method comprising preparing a medicament with the isolated protein or glycoprotein as claimed in claim 1, and administering an effective amount of said medicament to a patient in need thereof.

6. The method of claim 5, wherein said effective amount is between 0.1 mg and 10 mg per dose unit.

* * * * *